United States Patent [19]
Bogue et al.

[11] Patent Number: 5,648,033
[45] Date of Patent: Jul. 15, 1997

[54] METHOD AND APPARATUS FOR RETAINING A FORMED COMPRESSION DOSAGE UNIT WITHIN A DIE CAVITY

[75] Inventors: Beuford Arlie Bogue, Broad Run; Garry L. Myers, Reston, both of Va.

[73] Assignee: Fuisz Technologies Ltd., Chantilly, Va.

[21] Appl. No.: 438,165

[22] Filed: May 9, 1995

Related U.S. Application Data

[63] Continuation-in-part of Ser. No. 276,244, Jul. 18, 1994, which is a continuation-in-part of Ser. No. 259,496, Jun. 14, 1994, abandoned, and Ser. No. 259,258, Jun. 14, 1994, which is a continuation-in-part of Ser. No. 133,669, Oct. 7, 1993, Pat. No. 5,597,416, and Ser. No. 119,974, Sep. 10, 1993, Pat. No. 5,518,551.

[51] Int. Cl.$^6$ ........................................ B29C 43/08
[52] U.S. Cl. .................. 264/109; 264/123; 425/344; 425/345; 425/352; 425/353
[58] Field of Search .................... 264/109, 120, 264/123; 425/344, 345, 347, 350, 348 R, 352, 353

[56] References Cited

U.S. PATENT DOCUMENTS

| | | | |
|---|---|---|---|
| 2,068,619 | 1/1937 | Bailey | 107/17 |
| 2,214,505 | 9/1940 | Magnenat | 18/16 |
| 2,582,922 | 1/1952 | Crowley et al. | 425/356 |
| 3,332,367 | 7/1967 | Sperry et al. | 425/345 |
| 4,376,111 | 3/1983 | Tovey | 424/15 |
| 4,493,822 | 1/1985 | Tovey | 424/15 |
| 4,880,373 | 11/1989 | Balog et al. | 425/149 |
| 4,943,227 | 7/1990 | Facchini | 425/345 |
| 5,378,416 | 1/1995 | Kishi et al. | 264/40.5 |

*Primary Examiner*—Mary Lynn Theisen
*Attorney, Agent, or Firm*—Hoffmann & Baron

[57] ABSTRACT

A method and apparatus is provided for the formation of a tablet from tableting feedstock. An elongate die is provided which has a cavity defined by an inner wall. A pair of die punches are insertably positioned within the cavity. The die punches include opposed facing surfaces for supporting therebetween tableting feedstock. The die punches are relatively movable within the cavity to a tablet forming position to compress the feedstock into a tablet. The tablet forming positions defined by the facing die punch surfaces are spaced apart sufficient distance so as to maintain the formed tablet in contact with the inner wall of the cavity so as to retain the tablet within the cavity upon removal of the die punches.

19 Claims, 8 Drawing Sheets

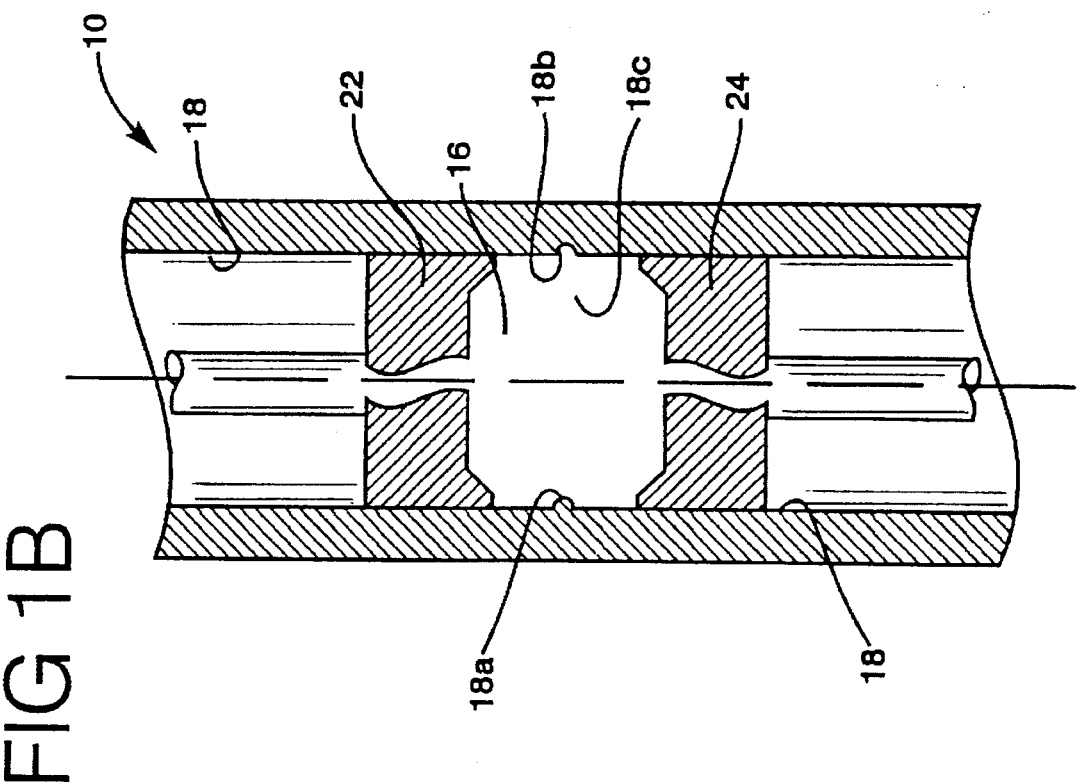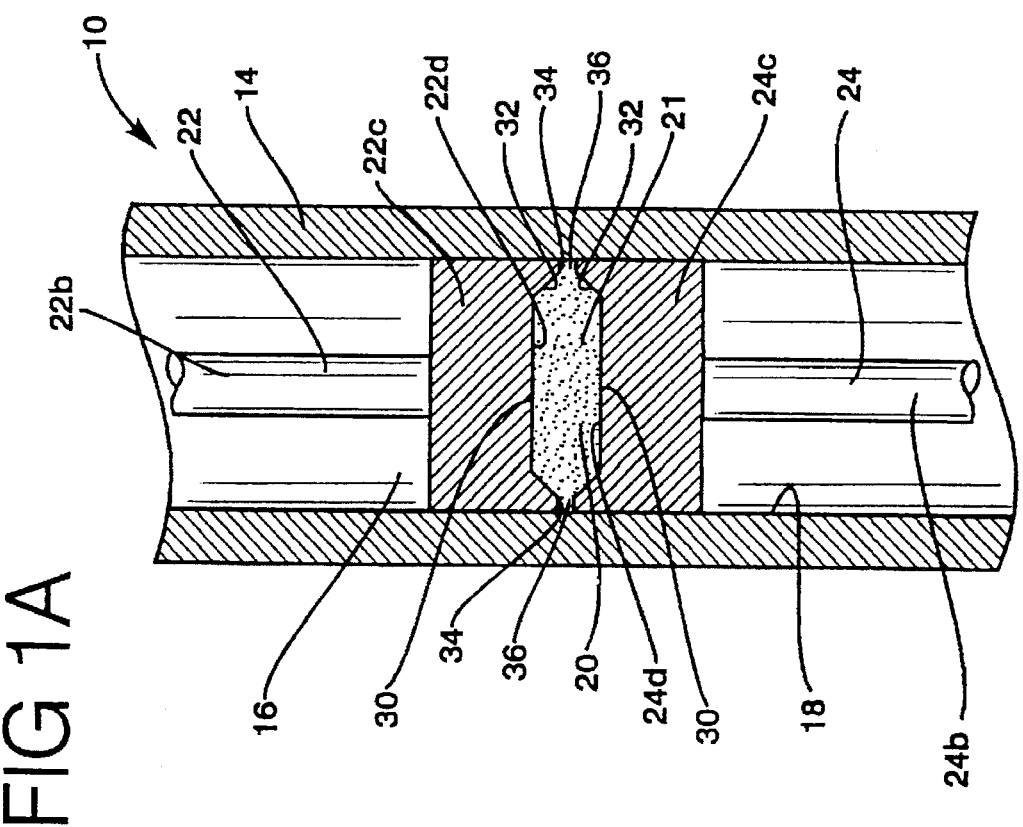

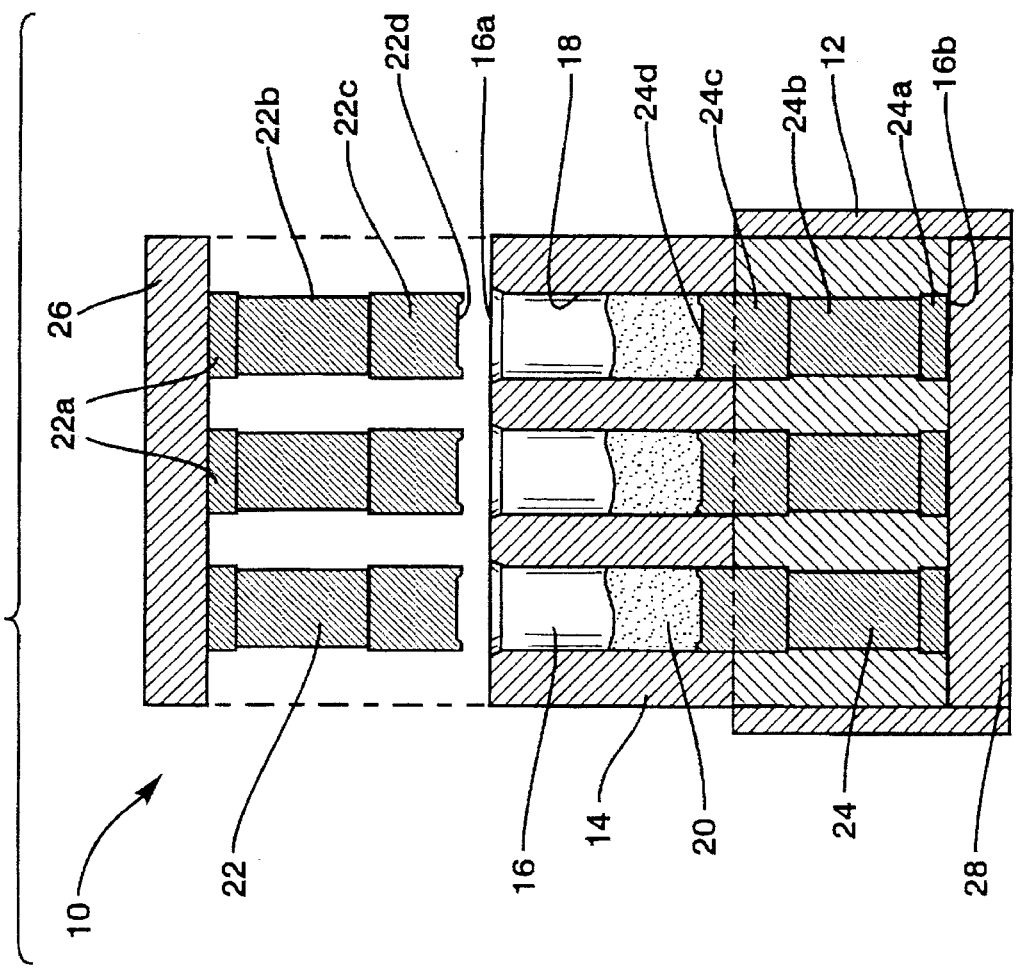

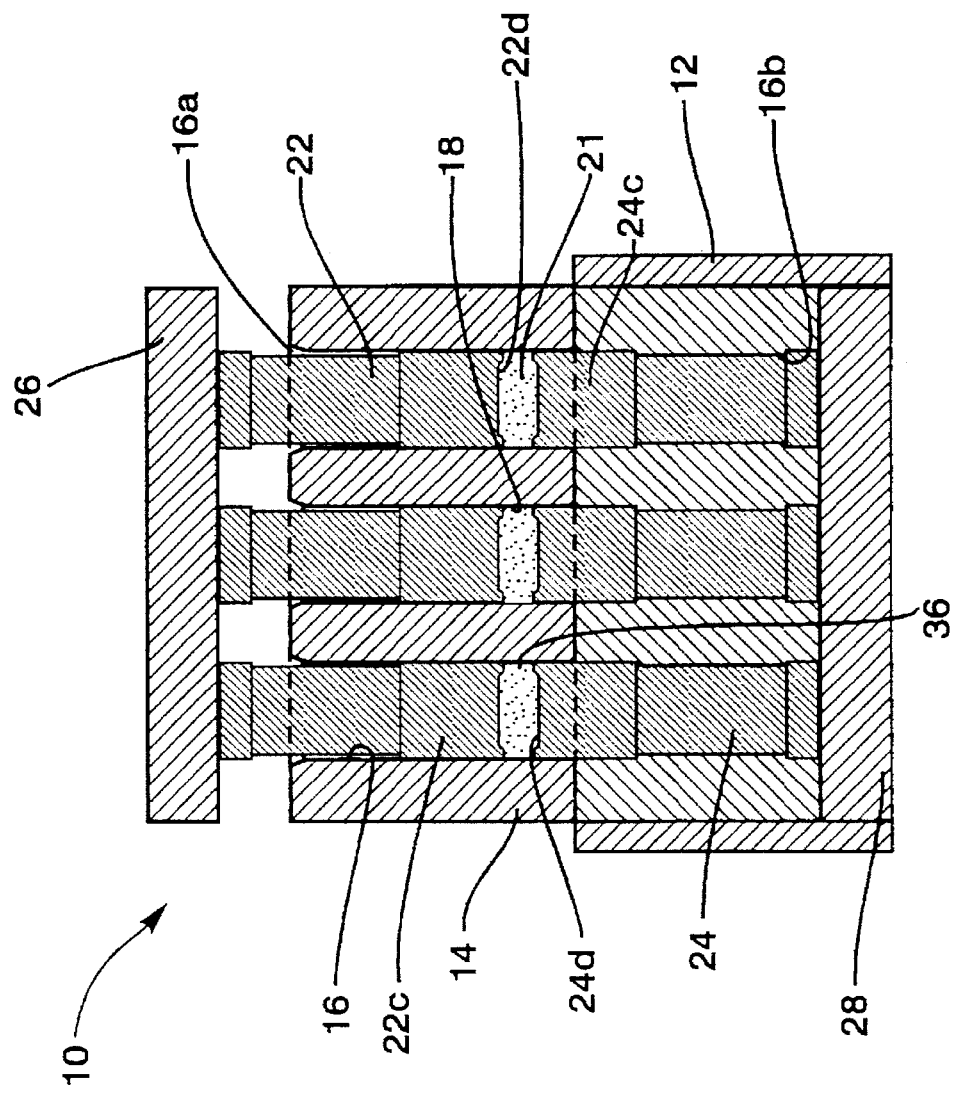

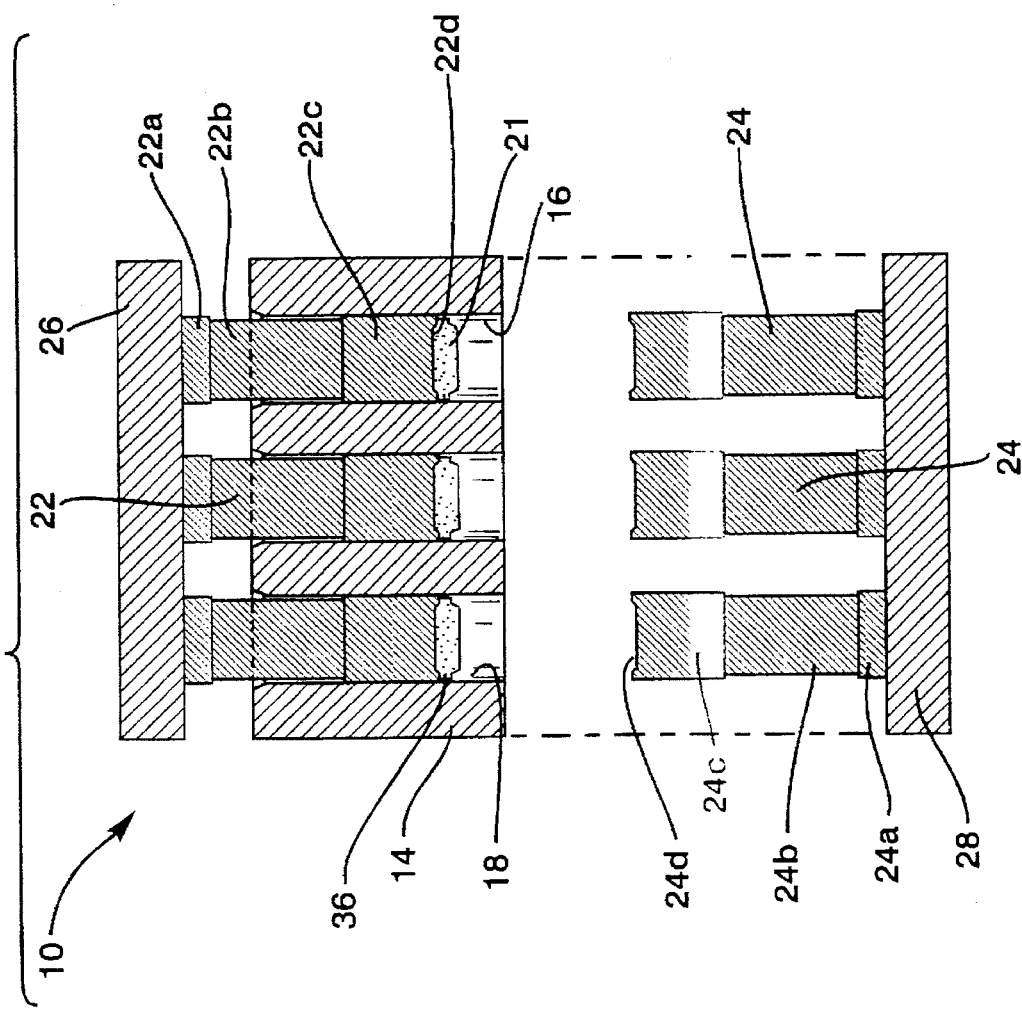

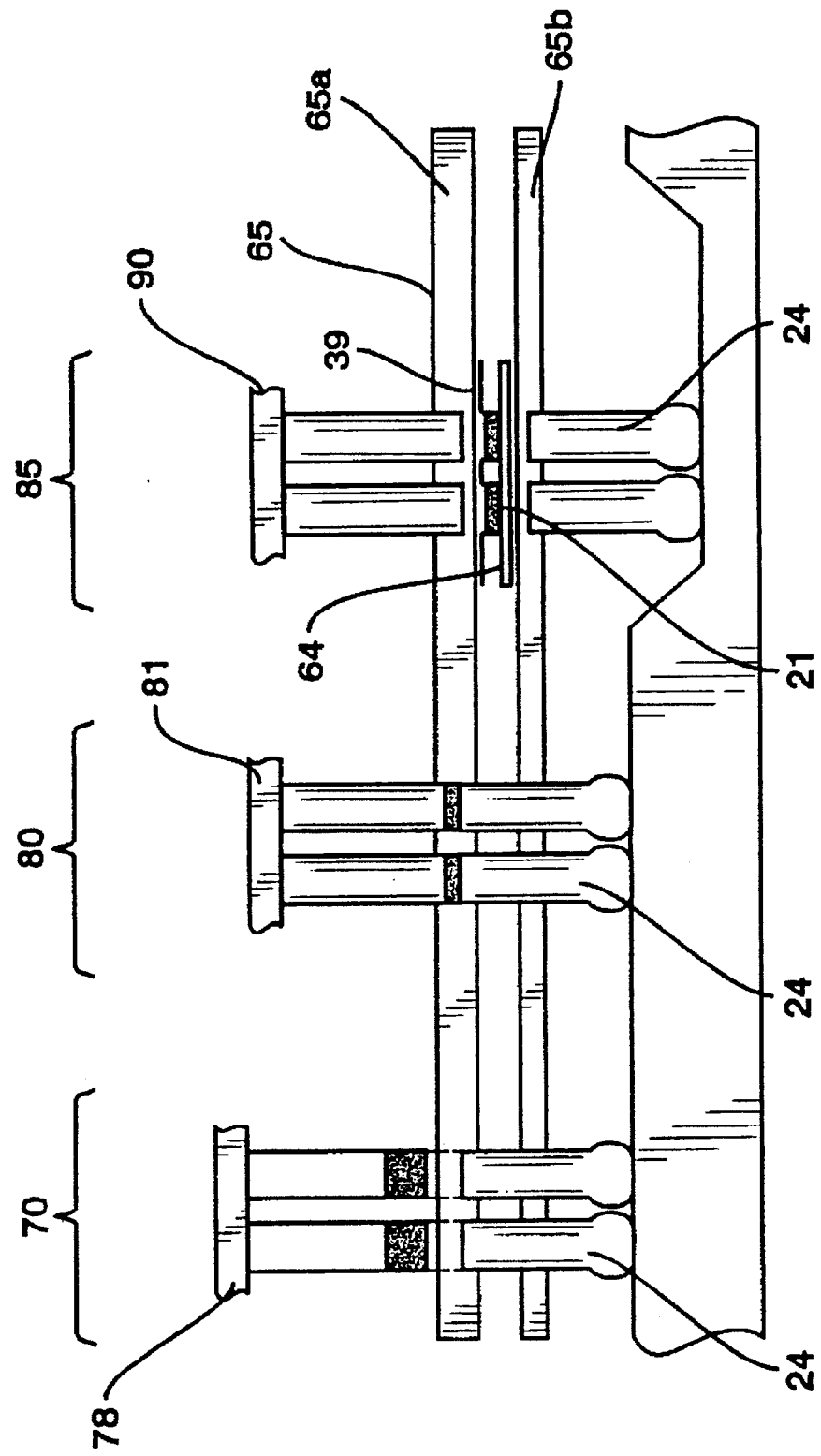

METHOD AND APPARATUS FOR RETAINING A FORMED COMPRESSION DOSAGE UNIT WITHIN A DIE CAVITY

CROSS REFERENCE TO RELATED APPLICATIONS

The present application is a continuation-in-part of U.S. application Ser. No. 08/276,244 filed Jul. 18, 1994 (Attorney's Docket No. 447-103) which is a continuation-in-part of U.S. application Ser. No. 08/259,496 filed Jun. 14, 1994 (Attorney's Docket No. 447-105) now abandoned, and U.S. application Ser. No. 08/259,258 filed Jun. 14, 1994 (Attorney's Docket No. 447-106), which is a continuation-in-part of U.S. application Ser. No. 08/133,669 filed Oct. 7, 1993 (Attorney's Docket No. 447-66) now U.S. Pat. No. 5,597,416 and U.S. application Ser. No. 08/119,974 filed Sept. 10, 1993 (Attorney's Docket No. 447-85) now U.S. Pat. No. 5,518,551. The contents of each of these co-pending, commonly-owned applications is incorporated herein by reference.

FIELD OF THE INVENTION

The present invention relates generally to a method and apparatus for forming compression dosage units, more specifically tablets. The present invention more particularly relates to forming tablets, preferably low density tablets, from tableting feedstock within a die cavity and maintaining the tablet in proper position in the die cavity enabling transfer of the tablet.

BACKGROUND OF THE INVENTION

Dosage units in the form of tablets are prepared by compressing a formulation containing a medicinal substance or drug and other ingredients, such as excipients selected for properties which enhance the production and use of the tablet. There are currently three known basic methods for preparing tablet granulations. These are wet granulation, dry granulation and direct compression. Both wet and dry granulations involve the formation of an agglomerate for feeding to a die cavity. Direct compression usually involves compressing a powder blend of an active ingredient with suitable excipients.

Other methods of preparing feedstock for preparing compression dosage units have been disclosed in the above-referenced copending applications as well as in copending, commonly owned U.S. application Ser. No. 08/194,682 filed Feb. 10, 1994. Each of these applications are incorporated herein by reference.

U.S. application Ser. No. 08/194,682 discloses a method of making a solid comestible by compressing shearform matrix masses sufficiently to form a comestible compression unit. U.S. application Ser. No. 08/259,496 discloses a method of preparing a quick dissolve low density comestible unit by mixing uncured shearform matrix and an additive, molding a unit dosage form therefrom, and curing the shearform matrix. Finally, U.S. application Ser. No. 08/259,258 discloses a method of preparing quick dissolve comestible units by initiating crystallization of shearform matrix, and combining, either before or after initiating crystallization, an additive with the shearform matrix to form flowable, compactible micro-particulates. Finally, the micro-particulate medium is compacted to form the quick dissolve comestible unit. In each of these disclosures, the tableting medium is prepared initially by use of shearform matrix. In most cases a quick dissolve tablet can be produced by providing a compressed body which is of low density and capable of being disintegrated and dispersed relatively rapidly, and in many cases, instantaneously.

Tableting processes known today in the art generally include the use of a machine which includes opposed upper and lower punches and die cavities positioned between the punches into which a tableting medium can be directed and subjected to compression between the punches. See, for example, U.S. Pat. No. 4,943,227; U.S. Pat. No. 4,880,373; U.S. Pat. No. 2,214,505 and U.S. Pat. No. 2,068,619. Other references which disclose different shapes of dosage units are U.S. Pat. No. 4,493,822, U.S. Pat. No. 4,376,111, and an excerpt from The Consumer Guide for "Prescription Drugs," p. 194–208, Publications International, Ltd. (1990).

The tablets which are formed in the die cavities must be transferred from the die to a package for ultimate distribution and sale. Typically after formation of the tablet, the upper and/or lower punches are removed from the cavity. In the manufacture of low density tablets, the tablets are retained in the cavities for transference to a further manufacturing station where the tablets are ejected into a package. However upon removal of the upper and lower punches the tablet is no longer captively retained in a die cavity. Further, as the upper and lower punches form a tight fit within the die cavity in order to properly form the tablet therein, removal of the punches creates a vacuum which tends to pull the tablet out from the cavity, or skew the tablet in the cavity. Such movement of a low density tablet in the die cavity makes the smooth transfer to a package more difficult.

It is therefore desirable to provide a method and apparatus for enabling the formation of low density tablets in a die cavity and the retention of the tablets in proper position within the cavity after formation and during transference.

SUMMARY AND OBJECTS OF THE INVENTION

It is an object of the present invention to provide a method and apparatus for forming a tablet, preferably a low density tablet, from tableting feedstock. The method provides for the formation of a tablet from tableting feedstock within a die having a die cavity including an internal wall. Tableting feedstock is deposited within the die cavity. First and second die punches are positioned within the die cavity to accommodate the feedstock between the die punches. Each of the die punches includes a tablet forming die punch surface having a central recess and a perimetrical ridge. The first die punch is moved towards the second die punch to a tablet forming position with respect thereto to compress the feedstock into a formed tablet therebetween. During movement of the first die punch toward the second, the die punch surfaces are maintained spaced from each other in the tablet forming position so that the opposed perimetrical ridges form a tablet edge in contact with the inner wall of the die cavity. It is further contemplated that the second die punch may be removed from the cavity while maintaining the tablet in contact with the inner wall of the die cavity. The first die punch may be then further moved within the die cavity to eject the formed tablet therefrom.

In its apparatus aspect, the present invention provides an apparatus for forming a tablet from tableting feedstock. The apparatus includes an elongate die having a cavity defined by an inner wall. A pair of die punches are insertably positioned within the cavity. The die punches include opposed facing die punch surfaces for supporting therebetween the tableting feedstock. The die punches are relatively movable within the die cavity to a tablet forming position to compress the feedstock between the die punch surfaces and into a formed tablet. Each die punch surface includes a raised perimetrical ridge. The tablet forming position is defined by the perimetrical ridge of the facing die punch surfaces being spaced apart a sufficient distance so as to form the tablet with a perimetrical edge in frictional engagement with the inner wall of the die cavity.

BRIEF DESCRIPTION OF THE DRAWINGS

FIG. 1A is a schematic representation of a formed tablet positioned within a die cavity.

FIG. 1B shows further embodiments of the inner wall of the die cavity of FIG. 1A.

FIG. 2 is a front plan view of the combination of a die cavity and upper and lower die punches of the present invention shown in an open position.

FIG. 3 shows the combination of FIG. 2 in a closed or tablet forming position.

FIG. 4 shows the combination of FIG. 3 with the lower die punches removed from the die cavity.

FIG. 7 and 8 are a top plan and side elevational schematic views of a portion of the apparatus of FIG. 6.

DETAILED DESCRIPTION OF THE PREFERRED EMBODIMENT

Figure 5:
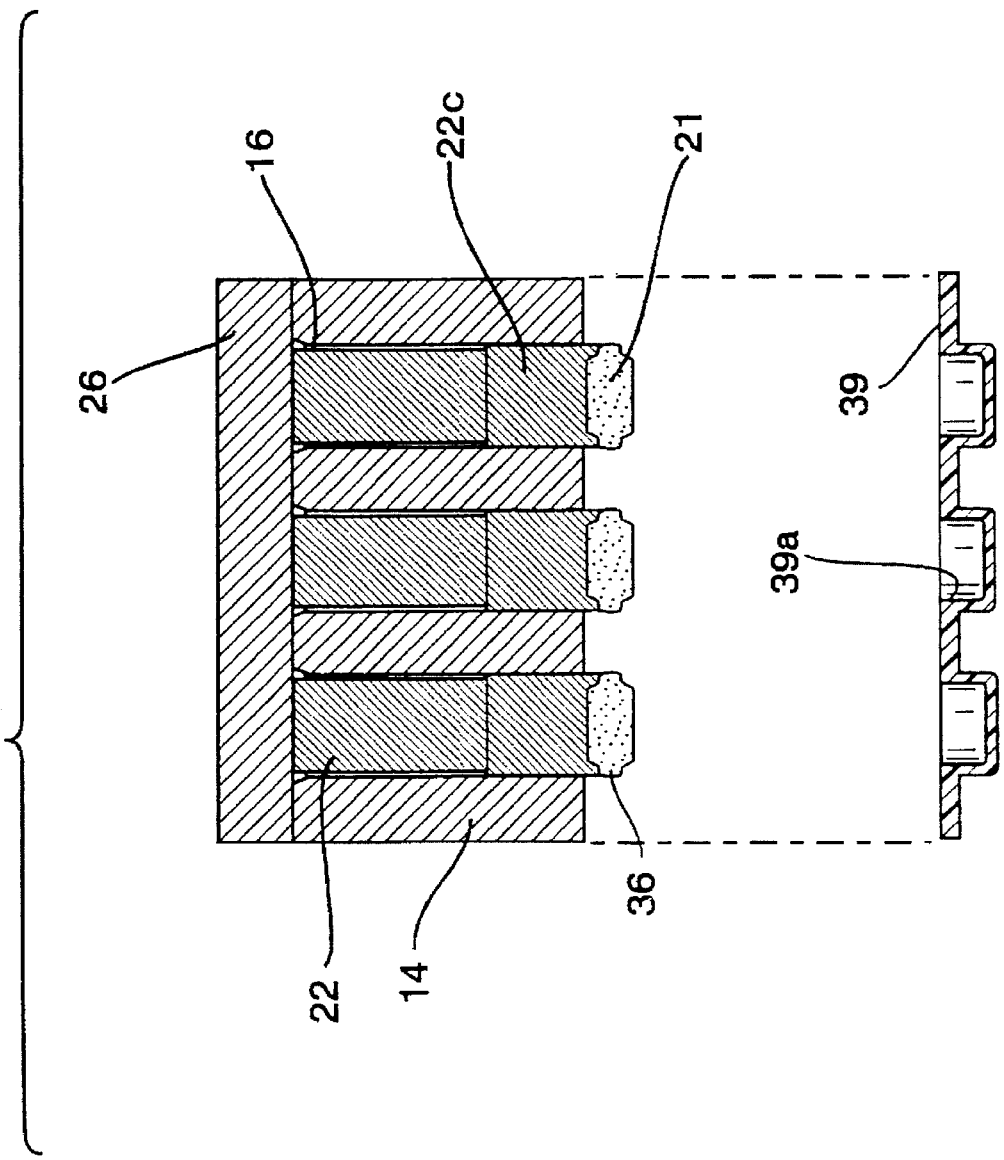
FIG. 5 shows tablets formed in accordance with the present invention being deposited into a product package.

The present invention provides a unique method and apparatus for preparing compression dosage units, such as tablets, in a die cavity and for maintaining the tablet within the die cavity for transfer to a package for further processing. The term "tablet" is used herein to mean a unit having two sides, sometimes referred to as a top and a bottom, and a continuous edge which joins the top and the bottom. The entire mass of the material throughout the tablet is the "volume" of the tablet.

The mass of the units prepared in accordance with the present invention is continuous in the sense that the feedstock material used to prepare the units ("tableting feedstock") is prepared in a single compression chamber ("die"), but which may have two different densities. The die cavity supports a pair of opposed compressors, sometimes referred to as a "die punches". A first volume is associated with the edge in that it circumscribes the unit and includes the edge surface. A second volume, which is referred to as the "non-edge" portion, is within the edge portion. In the present illustrative example the tableting feedstock is compressed and formed within the die cavity in such a manner that it is retained in the die cavity after formation of the tablet. This facilitates the ability to transfer the tablet for further processing.

The method and apparatus of this invention are especially useful in making low density tablets and preferably tablets which undergo further curing or processing to form a rigid structure. The term dow density is sued herein to denote tablets wherein at least 60% and preferably 80% of the volume of the tablet has a density of less than 1.2 grams per cubic centimeter and preferably less than 0.8 grams per cubic centimeter. For preferred embodiments, the apparatus and process of the present invention are used to make high porosity tablet which have a porosity of 0.35 to 0.75 and preferably 0.45 to 0.65. Porosity as used herein is defines as: 1-(bulk density÷actual density).

The non-edge portion of units prepared in accordance with the invention has a lower density, mass per unit volume, than the edge portion. The non-edge volume density is less than about 1.2 grams per cubic centimeter, preferably less than 0.8 grams per cubic centimeter, and most preferably not greater than 0.6 grams per cubic centimeter.

The edge portion of tablets prepared according to the invention can have a higher density than the non-edge portion. The edge portion has a density which is at least about 10% greater than the density of the non-edge portion, preferably about 15% greater, and most preferably about 20% greater. Thus, if the density of the non-edge portion is about 0.6 grams per cubic centimeter, the density of the edge portion is preferably about 0.66 grams per cubic centimeter, preferably about 0.69 grams per cubic centimeter, and most preferably about 0.72 grams per cubic centimeter.

The extent of the edge portion is that amount of volume and surface sufficient to increase the "strength" of the unit for handling by processing machinery and personnel without deterioration of the unit. "Strength" includes both resistance to unit fracture and surface crumbling, i.e., friability.

A tableting feedstock material which is particularly useful in the present invention is saccharide based. Particularly useful feedstocks for the tableting process of this invention are disclosed in U.S. application Ser. No. 08/259,496 (Attorney Docket No. 447-105) and U.S. application Ser. No. 08/259,258 (Attorney Docket No. 447-106).

In another embodiment, the feedstock disclosed in U.S. application Ser. No. 08/194,682 filed Feb. 10, 1994 (Attorney Docket No. 447-80), which includes a free form agglomerate wherein selected ingredients such as a medicinal substance, and a carrier are fused together, is used in the process of the present invention. The free form agglomerate is distinguished from agglomerates formed from wet and dry granulations. The components of the tablet are thoroughly dispersed throughout the product because the mixture attained in the free form agglomerate is microstructurally stabilized against migration out of mixture. Fusion of the ingredients in a micro-structurally-stabilized mixture is achieved prior to compression as a result of flash flow processing. The feedstock includes a saccharide-based material which acts as a carrier for the medicament.

Preferred materials useful as matrices may be chosen from such classes as sugars or sugar derivatives. The term sugar is meant to include those carbohydrates having a high glucose profile. A high glucose profile means that the carbohydrate has a large number of six-carbon mono and disaccharides as well as other glucose-based oligomers. Mono-, di-, tri- and polysaccharides and their derivatives may be employed. Examples include glucose, sucrose, maltose, lactose, arabinose, xylose, ribose, fructose, mannose, pentose, galactose sorbose, dextrose, sorbitol, xylitol, mannitol, pentatol, maltitol, isomalt, sucralose and mixtures thereof.

The carrier material can be selected from material which is capable of undergoing both physical and/or chemical changes associated with flash-flow processing. Materials useful as matrices may be chosen from those carbohydrates which are capable of forming free-form agglomerates upon being processed. Maltodextrins are an example of such carrier materials. Maltodextrins include those mixtures of carbohydrates resulting from hydrolysis of a saccharide feedstock which are described as solids having a DE of less than 45.

Polydextrose is also contemplated for use as a carrier. Polydextrose is a non-sucrose, essentially non-nutritive carbohydrate substitute. It can be prepared through polymerization of glucose in the presence of polycarboxylic acid catalyst and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers. Regarding polydextrose, Applicants incorporate herein the contents of copending U.S. application Ser. No. 07/881,612 filed May 12, 1992 (Attorney Docket No. 447-46) now abandoned.

The feedstock can also include maltooligo-saccharide produced by selective hydrolysis of cornstarch followed by removal of high and low molecular weight compounds. The general description of malto-oligosaccharides as contemplated herein is set forth in above-identified U.S. application Ser. No. 07/847,595 now abandoned.

The present invention is directed to the ability to form a feedstock tablet within a die cavity and to retain the formed tablet within the cavity after removal of one or more dies so as to permit transference of the formed tablet for further processing. It is especially important when making a low density tablet to maintain the structure of the tablet during transfer of the tablet to a location where it will be cured to a more rigid structure. This is accomplished in the present invention by constructing the die and die cavity in such a manner that the tablet is frictionally retained within the die cavity upon removal of one or more of the dies.

Referring to FIG. 1A, a schematic depiction of a die assembly 10 used to form a tablet 21 from tableting feedstock 20 is shown. In the schematic depiction, a single cavity 16 includes an upper die punch 22 and lower die punch 24. Each die punch 22, 24 preferably includes a generally cylindrical body 22b, 24b and tablet forming members 22c, 24c at opposed ends of cylindrical body 22b, 24b. However, other shaped die punches can be used to make tablets of non-cylindrical shapes. The position of the respective die punches is such that a tablet 21 may be formed from tableting feedstock 20 by appropriate movement of die punches 22 and 24. Each tablet forming member 22c, 24c is constructed to include a particular configuration of the tablet forming face 22d, 24d. In a preferred embodiment, the tableting forming faces are generally circular thus forming a circular tablet. However, it is within the contemplation of the present invention to form tablet forming faces of different configuration such as oval, spherical, square or any other shape desired. Each face includes a central recessed portion 30 and an extending outwardly tapered perimetrical sidewall 32 which terminates in a generally horizontal annular ridge 34. When tablet forming member 22c and 24c are moved to a tablet forming position shown in FIG. 1A, the respective ridges 34 are maintained in spaced apart relationship. The tablet 21 formed by such positioning thereby includes an outwardly extending annular tablet edge 36 which is compressed into contact with inner wall 18 of cavity 16. The tablet edge 36 has a vertical expanse which is less than the major vertical expanse of the tablet 21 as measured between each recessed portion 30 of the die face. Edge 36 has sufficient expanse to permit the tablet to frictionally engage inner wall 18 to hold the tablet therein upon removal of die punches 22 and 24 from cavity 16. In order to properly form tablet 21 therein, the tablet forming members 22c, 24c of die punches 22 and 24 are configured to tightly fit within cavity 16 engaging the inner wall 18 therealong. Upon removal of one or both of die punches 22 and 24 a slight vacuum may be created. Such a vacuum has a tendency to pull the formed tablet 21 out from cavity 16 or at least skew the tablet therein so that it is no longer in proper position. This makes the transfer of the formed tablet to a further processing location within the tablet forming machine difficult.

In the formation of low density tablets, once the tablet is formed within the die, a formed tablet must be moved to a further location where further processing such as packaging may take place. If the formed tablet 21 is not properly retained within the die cavity the difficulty of such transfer is increased. By providing a tablet edge 36 by the appropriate formation and positioning of die punches 22 and 24, the tablet 21 will be properly retained within cavity 16 upon removal of one or more die punches 22 and 24 so that the tablet 21 may be properly ejected into a package for further processing.

Additionally, as shown in FIG. 1B it is contemplated that by proper selection of the configuration of the inner cylindrical wall of the die cavity, as well as proper selection of the tableting feedstock, the compressed tablet may be directly frictionally retained within the die cavity 16 upon removal of the die punches. Such cavity configuration may include the inner cylindrical wall 18 having one or more annular frictional protrusions (ridges) 18a, recesses 18b or other surface configurations thereon so as to provide sufficient frictional resistance to retain the formed tablet therein upon removal of the die punches.

Frictional surfaces may also be formed by forming a roughened surface achieved by sand blasting, knurling or the like. Such frictional surface is located at an area 18c of the die cavity 16 where tablet formation occurs. The frictional surface, such as a ridge or recess, would impart a slight complementary structure on the formed tablet, This interference, while slight, is sufficient to retain the tablet in the die cavity.

Referring to FIGS. 2–5, a preferred embodiment of the present invention is shown. Die assembly 10 includes a housing 12 which supports a multi-cavity die 14. Housing 12 may be supported on or is part of a movable table which forms part of the tablet forming machine. Housing 12 accommodates a forming block or die 14 in fixed position for movement along therewith during the tableting process. Die 14 is a multi-cavity die which, in the present embodiment, includes a plurality of elongate generally cylindrical cavities 16 each having an inner cylindrical wall 18 and a pair of opposed open ends 16a and 16b. Each cavity 16 accommodates therein a preselected amount of tableting feedstock 20. The inner wall 18 of cavity 16 is configured to accommodate, through the opposed open ends 16a and 16b thereof, a pair of oppositely facing die punches 22 and 24. As shown in the drawings, upper die punches 22 and lower die punches 24 are provided in number corresponding to the number of cavities 16 of multi-cavity die 14. Each set of upper and lower die punches 22 and 24 are affixed to respective bases 26 and 28 which mutually support die punches 22 and 24 for uniform movement therewith.

In the present illustrative embodiment, each of upper die punches 22 and lower die punches 24 are of identical construction. However the present invention is not limited thereto. It is within the contemplation of the present invention to form upper die punch 22 of differing configuration from lower die punch 24 as will be described in further detail hereinbelow. Each of die punches 22 and 24 shown in FIG. 2, are elongate rod-like elements having proximal portions 22a, 24a affixed to bases 26 and 28. Each die punch includes an elongate cylindrical body 22b, 24b and a distally located tablet forming member 22c, 24c. Each tablet forming member is constructed to frictionally fit within cavity 16 of die 14 to slide against inner wall 18. Tablet forming member 22c, 24c includes tablet forming face 22d, 24d formed in a manner shown and described above with respect to FIG. 1. Each of faces 22d and 24d of opposed upper die punch 22 and lower die punch 24 are in facing opposition so as to support the tableting feedstock 20 therebetween upon insertion of die punches 22 and 24 into cavity 16.

Typically in tablet forming machines, the array of upper and lower die punches 22 and 24 supported on bases 26 and 28 are movable vertically towards and away from one another by an appropriate mechanism. The die punches are movable into and out of cavities 16 of die 14 in response to sequential operation of the tablet forming machine. Prior to movement of the die punches 22 and 24, tableting feedstock 20 is deposited within cavity 16. In order to facilitate such positioning, lower die punches 24 may be inserted into cavity 16 through lower open end 16b to a position shown in FIG. 2. Feedstock 20 may then be dispensed into cavities 16 through open upper end 16a. Any of a variety of filling wands or other structures may be used to deposit feedstock 20 into die cavities 16. It is further contemplated that a tablet preform formed from tableting feedstock may be deposited within die cavity 16. The formation of tablet preform is more fully described hereinbelow.

Thereafter, as shown in FIG. 3, upper die punches 22 may be moved in unison into cavities 16 through open end 16a. The feedstock 20 supported between the tablet forming members 22c and 24c in each cavity 16 is thereby formed into a tablet 21. The desired density of the tablet may be selected by appropriately controlling the relative movement of upper die punches 22 and lower die punches 24. Such control can be affected by either controlling the distance that the respective punches move or by controlling the force applied to the punches. Either manner may be effectively employed to consistently control the density of the tablet formed between the upper and lower die punches.

As above described, the construction of tablet forming members 22c and 24c provides for tablet formation with tablet 21 including an annular tablet edge 36 in contact with the inner wall 18 of cavity 16. This frictional engagement between the tablet 21 and the wall of cavity 16 allows the tablet 21 to be frictionally retained within the cavity 16 upon removal of lower die punches 34 therefrom.

Referring now to FIG. 4, in order to move the formed tablets 21 to a further location for subsequent processing such as placing tablets 21 in a package, as will be described in further detail hereinbelow, the lower die punches 24 supported on base 28 are removed from the individual cavities 16 of die 14. Upon such removal, tablets 21 by virtue of frictional ridge 36 remain positioned within cavity 16. This permits the easy transfer of the newly formed tablets 21 to a further location without risk of the tablets becoming dislodged from die 14.

As shown in FIG. 5, die 14 including the array of upper die punches 22 may be moved to a further location where the formed tablets held in the cavity 16 may be transferred to a package. Tablet package 39 is generally a planar member formed of suitable transparent plastic or other conventional materials which serve as the product tray for holding the tablets. Package 39 includes a plurality of tablet receiving cavities 39a which form wells to accommodate tablets 21. In the present illustrative embodiment cavities 39 are generally cup-shaped members which accommodate tablets 21. However it is contemplated that a package 39 may be formed having cavity shapes which more closely approximate the shape of tablet 21. Once die 14 is properly positioned over package 39 so that die cavities 16 are aligned with package cavities 39a, the array of upper die punches 22 may be moved downwardly towards die 14 to thereby cause ejection of tablets 21 from cavities 16. The tablets 21 are ejected into the individual cavities 39a whereupon the package 39 may be subject to secondary operations such as sealing, labeling and the like. Thus, the friction achieved between ridge 36 of tablet 21 and the walls 18 of die 16 is sufficient to hold the tablet 21 in position therein but may be overcome by movement of upper punches 24 so as to easily eject the tablets from die 14.

The present invention as depicted in FIGS. 2–5 may be used in combination with a variety of tablet forming machines. Such machinery would include a location where feedstock may be accumulated and would also provide for the transfer of accumulated feedstock to the die cavity for formation into tablets. An example of similar tablet forming machines are the type shown and described in commonly assigned, co-pending U.S. Pat. applications bearing Attorney Docket Numbers 447-123 Ser. No. 08/438239 and 447-125 Ser. No. 08/437300 which have been filed at even date with the filing of the present application and which are incorporated by reference herein.

Figure 6:
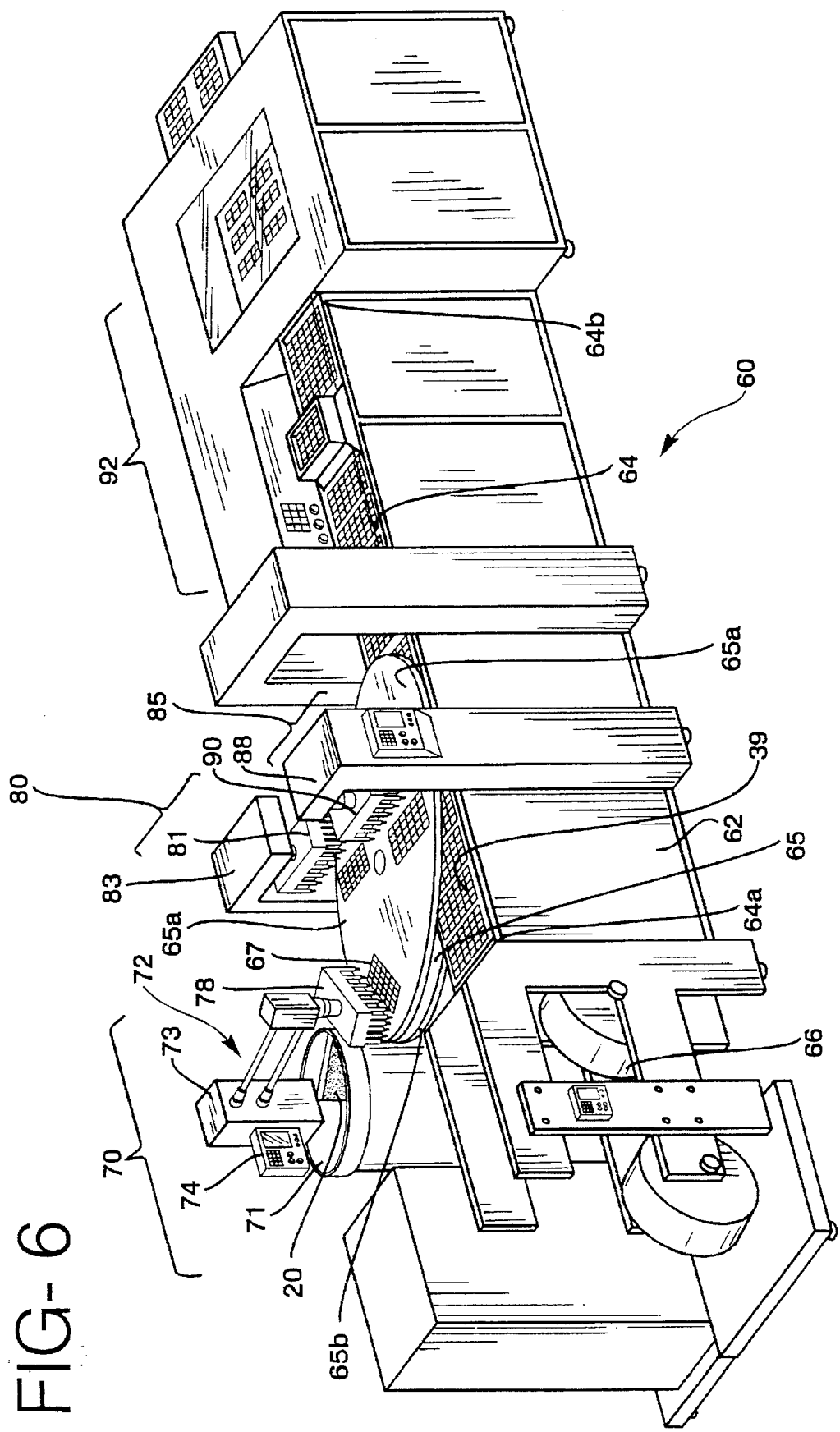
FIG. 6 shows a form, fill and seal apparatus of the present invention.
Figure 7:
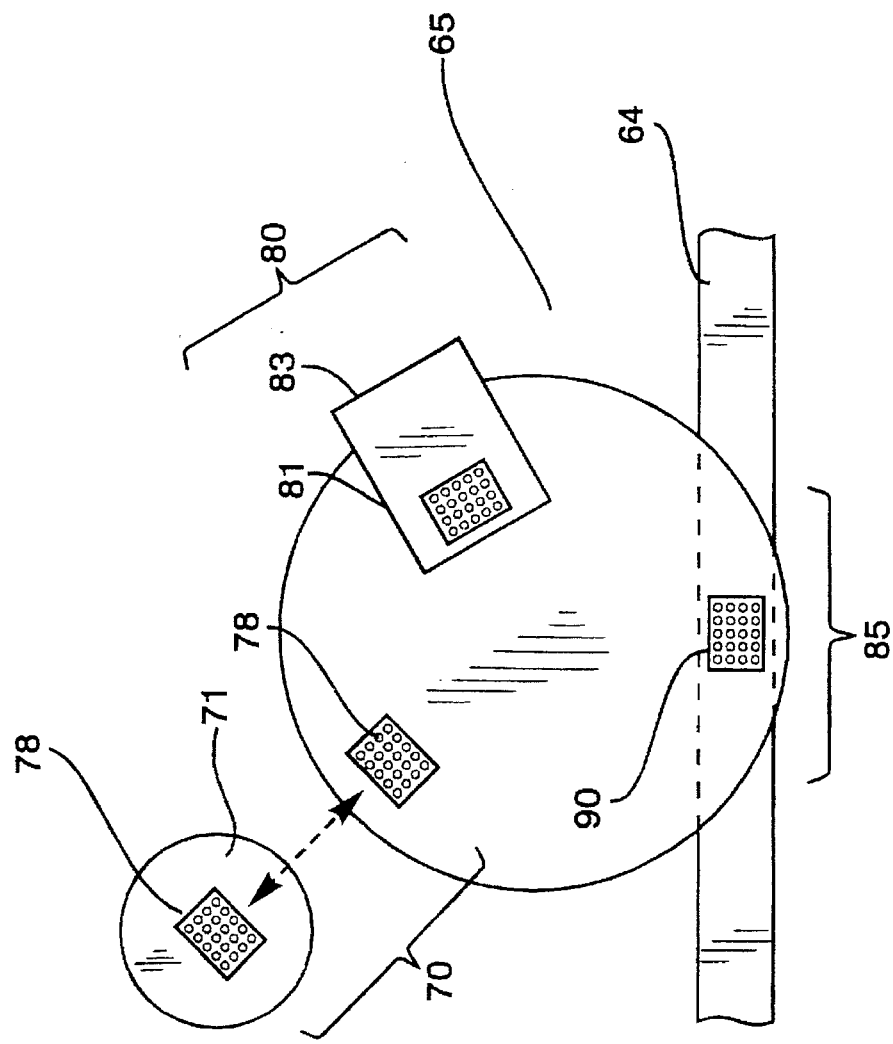

A particular tablet forming machine which employs the concept of the present invention is more fully shown and described in FIGS. 6, 7 and 8. Tableting apparatus 60 is a form, fill and seal machine designed for in-line operation in full production. Tableting apparatus 60 forms a tablet package from plastic sheeting, compresses a tablet from tableting feedstock, fills the package with formed tablets and seals the product package in a single continuous operation. Tableting apparatus 60 is a computer controlled automatic assembly apparatus which includes and elongate lower cabinet 62 having an upper longitudinal table 64 extending between ends 64a and 64b. Table 64 is linerally movable under the operation of electromechanical drive mechanisms (not shown) operated by one or more controllers. A roll of plastic sheeting 66 is fed into cabinet 62 where cavities 39 are formed in the sheeting. The cabinet 62 may contain a heating element and forming dies preferably a vacuum formed die (not shown) for formation of the multi-cavity product tray 39. Continuously joined product trays 39 of the type shown in FIG. 5 are positioned on table 64 for linear movement therealong. While not shown herein, table 64 may include thereon appropriately shaped support members for individually supporting one of the product trays 39. Apparatus 60 further supports a rotating table 65 adjacent longitudinal table 64. Table 65 includes a pair of spaced apart table surfaces 65a and 65b which accommodate therebetween longitudinal table 64. Upper table surface 64a includes at three spaced locations therearound, die arrays 67 including a forming block as individual die cavities of the type shown and described above with respect to FIGS. 2–5 which extend through table surface 65a and are open at either end. As will be further described hereinbelow, the rotation of table 65 causes the die arrays 67 to be sequentially indexed among positions which fill the die cavities with tableting feedstock, compress the feedstock into tablets and dispense the tablets into packages.

Tableting apparatus 60 defines a first station 70 adjacent end 64a of table 64. First station 70 defines a fill station for filling the die cavities of die array 67 with tableting feedstock 20 from an appropriate reservoir 71. A dispensing assembly 72 includes an operable support 73 controlled by a controller 74. A dispensing array 78 movably supported to support apparatus 73 provides for the accumulation of a premeasured amount of feedstock 20 from reservoir 71. The array 78 is then movable over die array 67 at which time the premeasured amount of feedstock dispensed into each of the individual cavities of die array 67. At this point, as shown in FIGS. 7 and 8, an array of lower die punches 24 supported between table surfaces 65a and 65b are positioned within the individual cavities of die array 67 in a manner similar to that shown in FIG. 2. The dispenser array 78 may be any array of devices which permits the accumulation of a premeasured volume of tableting feedstock and the dispensing of such feedstock into the individual cavities of die array 67.

Rotating table 65 is then rotated in a clockwise fashion as shown in FIG. 6 so that filled die array 67 is indexed to a second station 80. Second station 80 includes an overhead support apparatus 83 supporting an array 81 of upper die punches 22 of the type shown and described above with respect to FIGS. 2–5. At second station 80 the die punches 22 are moved in unison into the cavities of die array 67 so as to compress the feedstock held therein between the opposed die punch faces to form tablet 21 therein. The formation of tablet 21 is described in detail in FIGS. 2–5 hereinabove. After forming tablet 21 within die array 67, the rotating table 65 is again rotated in a clockwise fashion until the filled die array is positioned at third station 85. Third station 85 includes an overhead support apparatus 88 which supports an array of tablet dispensing elements 90 for vertical movement therewith. Array of dispensing elements 90 are configured to have a shape which may be accommodated within the cavities of die array 67 to dislodge the formed tablets 21 and eject the tablets into the cavities 39a of product tray 39 supported on longitudinal table 64.

As rotating table 65 is rotatably indexed among the first, second and third stations, the array of lower die punches are moved along therewith being retained by lower table surface 65b. A support surface 65c beneath table 65 (FIG. 8) supports lower die punches 24 for continuous movement with the rotation of table 65. As the die array 67 is indexed from second station 80 to third station 85, lower table surface 65b passes beneath longitudinal table 64. Support surface 65c supports the array of lower die punches 24 so that at third station 85 the die punches 24 drop out from die array 67 and pass beneath table 64 and the product package 39 supported thereon. A recessed portion 65d of support surface 65c permits such lower die punch movement. In this manner the formed tablets 21 will be supported within the cavities of die array 67 in a manner similar to that shown with respect to FIG. 4 where the array of upper die punches have also been removed. The tablets 21 are frictionally supported within the cavities of die array 67, as described above, until such time as they are dispensed from the cavities by insertion thereinto of the dispensing elements 90 at station 85.

Once the tablets 21 are dispensed into the cavities 39a of package 39, the filled product package 39 is moved along table 64 to subsequent stations in tablet forming apparatus 60. At one such subsequent station 90, inspection of the filled product trays may take place. Such inspection would include assuring that each cavity is filled with a tablet and that the tablets are of correct size and weight. After inspection has taken place, the product packages are moved along table 67 to one or more additional stations 92 where further secondary operations may take place. Such secondary operations may include operations such as curing the tablet by heat, steam, moisture or other means, placing a sealing lid over the product package, die cutting the package into individual units, as well as labeling the tablet or package (such as by ink jet printing, pad printing, gravure printing or other printing techniques) the package and boxing the package.

Various changes to the foregoing described and shown structures would now be evident to those skilled in the art. Accordingly, the particularly disclosed scope of the invention is set forth in the following claims.

What is claimed is:

1. An apparatus for forming a tablet from tableting feedstock comprising:

a die including an elongate die cavity for accommodating said feedstock, said die cavity having an inner wall and at least one open end; and first and second die punches each having a tablet forming die punch surface;

said first die punch being movably positionable within said die cavity and said second die punch being removably insertably positioned within said at least one open end of said die cavity, said die punch surfaces being in facing opposition;

said die punches being relatively movable within said die cavity to compress said tableting feedstock into said tablet between said die punch surfaces and into retentive engagement against said inner wall of said die cavity by said relative movement of said die punches to a tablet forming position;

whereby upon withdrawal of said die punches from said tablet forming position, said tablet remains in said retentive engagement with said die cavity inner wall.

2. An apparatus of claim 1 wherein said tablet forming position of said die punch is adjacent a tablet forming location of said inner wall of said die cavity.

3. An apparatus of claim 2 wherein said tablet forming location of said inner wall includes at least one frictional protrusion extending into said die cavity.

4. An apparatus of claim 2 wherein said tablet forming location of said inner wall includes at least one recess extending into said inner wall.

5. An apparatus for forming a tablet from tableting feedstock comprising:

a die including an elongate die cavity for accommodating said feedstock, said die cavity having an inner wall and at least one open end; and first and second die punches each having a tablet forming die punch surface;

said first die punch being movably positionable within said die cavity and said second die punch being removably insertably positioned within said at least one open end of said die cavity, said die punch surfaces being in facing opposition;

said die punches being relatively movable within said die cavity to compress said tableting feedstock into said tablet between said die punch surfaces and against said inner wall of said die cavity by said relative movement of said die punches to a tablet forming position;

said first and second die punch surfaces include a central recessed portion and a raised perimetrical ridge and wherein said raised perimetrical ridges of said opposed die punch surfaces form a tablet edge for frictionally retaining said tablet against said inner wall of said die cavity so as to retain said tablet within said cavity upon said removal of said second die punch from said cavity.

6. An apparatus of claim 5 wherein said frictional retaining means includes said tablet edge being formed in contact with said inner wall of said die cavity.

7. An apparatus of claim 1 wherein said die cavity inner wall is generally cylindrical.

8. An apparatus of claim 6 wherein said die punches are generally solid members and wherein said opposed facing die punch surfaces are generally configured into a tablet shape.

9. An apparatus of claim 8 wherein in said tablet forming position said raised ridges of said opposed die punch surfaces are maintained out of contact with one another.

10. An apparatus of claim 6 wherein said raised ridges of said opposed die punch surfaces are spaced apart in said tablet forming position a distance defining a vertical expanse of said tablet edge.

11. A method of forming a low density tablet from tableting feedstock comprising the steps of:

provoding a die having a die cavity defined by an inner wall;

depositing said tableting feedstock within said die cavity;

positioning a pair of die punches within said die cavity to accommodate said feedstock between said die punches;

moving said die punch toward the other said die punch to a tablet forming position to compress said feedstock into said tablet therebetween;

maintaining said one die punch spaced from said other die punch in said tablet forming position so as to form said tablet with a tablet edge in retentive frictional contact with said inner wall of said die cavity; and removing said other die punch from said cavity while maintaining said tablet within said cavity.

12. A method of claim 1 further including the step of ejecting said formed tablet from said cavity.

13. A method of claim 12 wherein said ejecting step includes further moving said one die punch after said removing step to push said formed tablet out of said die cavity.

14. A method of forming a low density tablet from tableting feedstock comprising the steps of:

providing a die having a die cavity defined by an inner wall;

depositing said tableting feedstock within said die cavity;

positioning a pair of die punches within said die cavity to accommodate said feedstock between said die punches wherein each said die punch includes a die punch surface including a central recess and a perimetrical ridge;

moving said die punch toward the other said die punch to a tablet forming position to compress said feedstock into said tablet therebetween; and maintaining said perimetrical ridge of one die punch surface spaced from the perimetrical ridge of the other die punch surface in said tablet forming position so as to form said tablet with a perimetrical reduced tablet edge in retentive frictional contact with said inner wall.

15. An apparatus for compressing tableting feedstock into a tablet comprising:

a die including an elongate die cavity for accommodating said feedstock, said die cavity having an inner wall and at least one open end; and first and second die punches each having a tablet forming die punch surface;

said first die punch being movably positionable within said die cavity and said second die punch being removably insertably positioned within said at least one open end of said die cavity, said die punch surfaces being in facing opposition;

said die punches being relatively movable within said die cavity to compress said tableting feedstock and urge said feedstock into frictional engagement with a portion of said cavity inner wall wherein said compressed feedstock is retained in frictional engagement with said cavity inner wall upon removal of both said die punches from engagement with the compressed tablet.

16. An apparatus of claim 15 wherein said portion of said die cavity inner wall includes frictional retention elements for engagement with said compressed feedstock.

17. An apparatus of claim 16 wherein said frictional retention elements include a protrusion extending from said inner wall portion.

18. An apparatus of claim 16 wherein said frictional retention elements include a recess in said inner wall portion.

19. An apparatus of claim 15 wherein each said die punch surface includes a central recessed portion and a raised perimetrical portion.

* * * * *